United States Patent
Gore et al.

(10) Patent No.: US 10,130,309 B2
(45) Date of Patent: *Nov. 20, 2018

(54) METHODS FOR DETERMINING PHYSIOLOGICAL PARAMETERS BASED ON ELECTRICAL IMPEDANCE MEASUREMENTS

(71) Applicant: General Electric Company, Schenectady, NY (US)

(72) Inventors: Amit Satish Gore, Glenville, NY (US); Jeffrey Michael Ashe, Gloversville, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/244,014

(22) Filed: Aug. 23, 2016

(65) Prior Publication Data

US 2016/0354041 A1 Dec. 8, 2016

Related U.S. Application Data

(63) Continuation-in-part of application No. 13/408,868, filed on Feb. 29, 2012, now Pat. No. 9,801,564.

(51) Int. Cl.
*A61B 5/0402* (2006.01)
*A61B 5/00* (2006.01)
(Continued)

(52) U.S. Cl.
CPC .......... *A61B 5/7282* (2013.01); *A61B 5/0531* (2013.01); *A61B 5/0816* (2013.01);
(Continued)

(58) Field of Classification Search
CPC .......... A61B 5/113; A61B 5/0402; G01S 8/56
See application file for complete search history.

(56) References Cited

U.S. PATENT DOCUMENTS 6,760,388 B2 * 7/2004 Ketchum ............. H04B 7/0417
375/295
7,479,911 B2 * 1/2009 Chakrabartty ........ H03M 3/466
341/143
(Continued)

FOREIGN PATENT DOCUMENTS

CN 102246082 A 11/2011

OTHER PUBLICATIONS

Chakrabartty, Gore, and Oweiss, "An adaptive multiple-input multiple-output analog-to-digital converter for high density neuroprosthetic electrode arrays," 2006, Proceedings of the 28th IEEE, pp. 656-659.*
Gore et al., filed Feb. 29, 2012, U.S. Appl. No. 13/408,868.
Unofficial English translation of Office Action issued in connection with corresponding DE Application No. 112013001215.4 dated Feb. 27, 2017.

*Primary Examiner* — Mischita Henson
*Assistant Examiner* — Christine Liao
(74) *Attorney, Agent, or Firm* — GE Global Patent Operation; Pabitra Chakrabarti (57) ABSTRACT

A system and method for determining physiological parameters based on electrical impedance measurements is provided. One method includes obtaining electrical measurement signals acquired from a plurality of transducers coupled to a surface of an object and spatially pre-conditioning the obtained electrical measurement signals. The method also includes performing multiple-input-multiple-output (MIMO) processing of the spatially pre-conditioned electrical measurement signals to correlate the spatially pre-conditioned electrical measurement signals to separate the electrical measurement signals.

16 Claims, 7 Drawing Sheets

(51) Int. Cl.
    *A61B 5/053*    (2006.01)
    *A61B 5/08*     (2006.01)
    *A61B 5/11*     (2006.01)
    *A61B 5/113*    (2006.01)
    *G16H 40/63*    (2018.01)

(52) U.S. Cl.
    CPC ............... *A61B 5/11* (2013.01); *A61B 5/113* (2013.01); *A61B 5/7207* (2013.01); *A61B 5/7225* (2013.01); *A61B 5/7275* (2013.01); *H05K 999/99* (2013.01); *A61B 5/0402* (2013.01); *A61B 5/7264* (2013.01); *G16H 40/63* (2018.01)

(56)            References Cited

U.S. PATENT DOCUMENTS

| | | |
|---|---|---|
| 8,120,845 B2 | 2/2012 | Brown et al. |
| 8,554,517 B2 * | 10/2013 | Fu .......................... G06F 19/18 600/524 |
| 2007/0142733 A1 * | 6/2007 | Hatlestad ............. A61B 5/0535 600/508 |
| 2010/0149633 A1 * | 6/2010 | Brown ................... G02B 7/004 359/407 |
| 2010/0225303 A1 | 9/2010 | Min et al. |
| 2011/0237939 A1 * | 9/2011 | Melamed ................. A61B 8/08 600/425 |

\* cited by examiner

METHODS FOR DETERMINING PHYSIOLOGICAL PARAMETERS BASED ON ELECTRICAL IMPEDANCE MEASUREMENTS

CROSS-REFERENCE TO RELATED APPLICATIONS

This application is a continuation-in-part of application Ser. No. 13/408,868 filed Feb. 29, 2012, now U.S. Pat. No. 9,801,564, issued Oct. 31, 2017; the disclosure of which is incorporated herein by reference in its entirety.

STATEMENT REGARDING FEDERALLY SPONSORED RESEARCH OR DEVELOPMENT

The United States Government may have certain rights in this invention pursuant to U.S. Government Contract Number R21 EB015608 awarded by the National Institutes of Health.

BACKGROUND

Continuous monitoring of respiratory rate or other biological signals can provide useful information for managing a patient's condition. For example, shortness of breath and difficulty in breathing are directly associated with deteriorating conditions in patients with heart failure (HF) and/or chronic obstructive pulmonary disease (COPD). The continuous monitoring of respiratory status in these patients can alert caregivers to administer early interventions to manage disease symptoms, which can prevent catastrophic events and improve quality of life.

However, continuous monitoring of respiratory rate or pattern is often not used in clinical practice due to the difficulty in performing these measurements, especially in non-intubated ambulatory settings. In particular, conventional measurement methods and systems that obtain data directly from the patient's airway are more accurate, but difficult to administer and often intolerable for patients. Conventional measurement methods and systems that rely on capturing chest motion often suffer from poor accuracy due to motion artifacts, thus making the measurements unsatisfactory for monitoring. For example, respiratory rate monitoring or monitoring of any biological signals requires the extraction of information from signals occurring within noise and attributing the information to the related biological event. These biological signals are often correlated and carry temporal and spatial information. The temporal signal may be obtained with conventional data acquisition systems (e.g., patient monitoring systems), but the spatial information requires enhanced digital signal processing when using the conventional systems. This digital signal processing requires additional processing resources including additional digital hardware and power to obtain or extract the spatial information. For example, redundant signals are needed for processing in conventional systems using principal component analysis (PCA) and independent component analysis (ICA) methods.

BRIEF DESCRIPTION

In accordance with an embodiment, a method for separating electrical measurement signals is provided. The method includes obtaining electrical measurement signals acquired from a plurality of transducers coupled to a surface of an object and spatially pre-conditioning the obtained electrical measurement signals either digitally after digitization or in analog before digitization. The method also includes performing multiple-input-multiple-output (MIMO) processing of the spatially pre-conditioned electrical measurement signals to correlate the spatially pre-conditioned electrical measurement signals to separate the electrical measurement signals.

In accordance with another embodiment, a method for monitoring breathing is provided. The method includes positioning a plurality of transducers on a surface of a person and obtaining electrical measurement signals from all or a subset of the plurality of transducers. The method also includes performing multiple-input-multiple-output (MIMO) processing of the electrical measurement signals to correlate the electrical measurement signals to separate the electrical measurement signals into breathing signals and ambulatory motion signals. MIMO processing is a specific example of hardware topology but certainly not restrictive. The same functionality can be obtained using analog or digital preconditioning before or after digitization respectively.

In accordance with yet another embodiment, an impedance measurement system is provided that includes a plurality of transducers configured for positioning at a surface of an object, wherein the plurality of transducers corresponds to a plurality of channels. The impedance measurement system also includes an excitation driver electrically coupled to at least a subset of the plurality of channels and configured to generate electrical excitations on at least a subset of the plurality of transducers, and a response detector configured to measure a response on at least a subset of the plurality of transducers to define electrical measurement signals. The impedance measurement system further includes a processor having a physiological parameter extraction module configured to use multiple-input-multiple-output (MIMO) processing of the electrical measurement signals to correlate the electrical measurement signals to separate the electrical measurement signals. As such, in accordance with an embodiment of the invention.

BRIEF DESCRIPTION OF THE DRAWINGS

The presently disclosed subject matter will be better understood from reading the following description of non-limiting embodiments, with reference to the attached drawings, wherein below.

DETAILED DESCRIPTION

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentalities shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a system and method for extracting/separating or distinguishing electrical measurements of interest, such as desired physiological signals of interest, from electrical measurements that are not of interest, such as electrical impedance signals of physiological or non-physiological signals and noise sources that are not of interest. For example, in some embodiments, electrical impedance signals due to desired physiological activities (e.g., breathing) are separated from electrical impedance signals due to undesired physiological activities (e.g., heart or ambulatory motion) and from undesired non-physiological signals (e.g., noise) to perform real-time continuous monitoring of physiological activities.

At least one technical effect is real-time continuous monitoring of physiological activities that may be performed using low complexity electronics and signal processing. For example, a patient monitor may be provided in accordance with various embodiments to measure electrical impedance to determine the respiration or breathing rate in comatose, sedated or sleeping patients, as well as in conscious patients exhibiting motion. At least one other technical effect is enhancing the quality of spatially correlated signals of interest. By practicing various embodiments, respiratory patterns may be classified, for example, classifying respiratory patterns in human subjects as normal breathing rates, distress conditions, breathing stoppage and body motion with breathing.

It should be noted that although various embodiments may be described in connection with an Electrical Impedance Spectroscopy (EIS) system or an Electrical Impedance Tomography (EIT) system having particular components, the various embodiments may be implemented in connection with any system that is capable of measuring electrical impedance of an object (e.g., a portion of a patient). Additionally, although the various embodiments may be described in connection with separating signals to identify respiratory rate separate from patient motion or other event artifacts, other physiological and non-physiological signals or activities may be separated.

Figure 1:
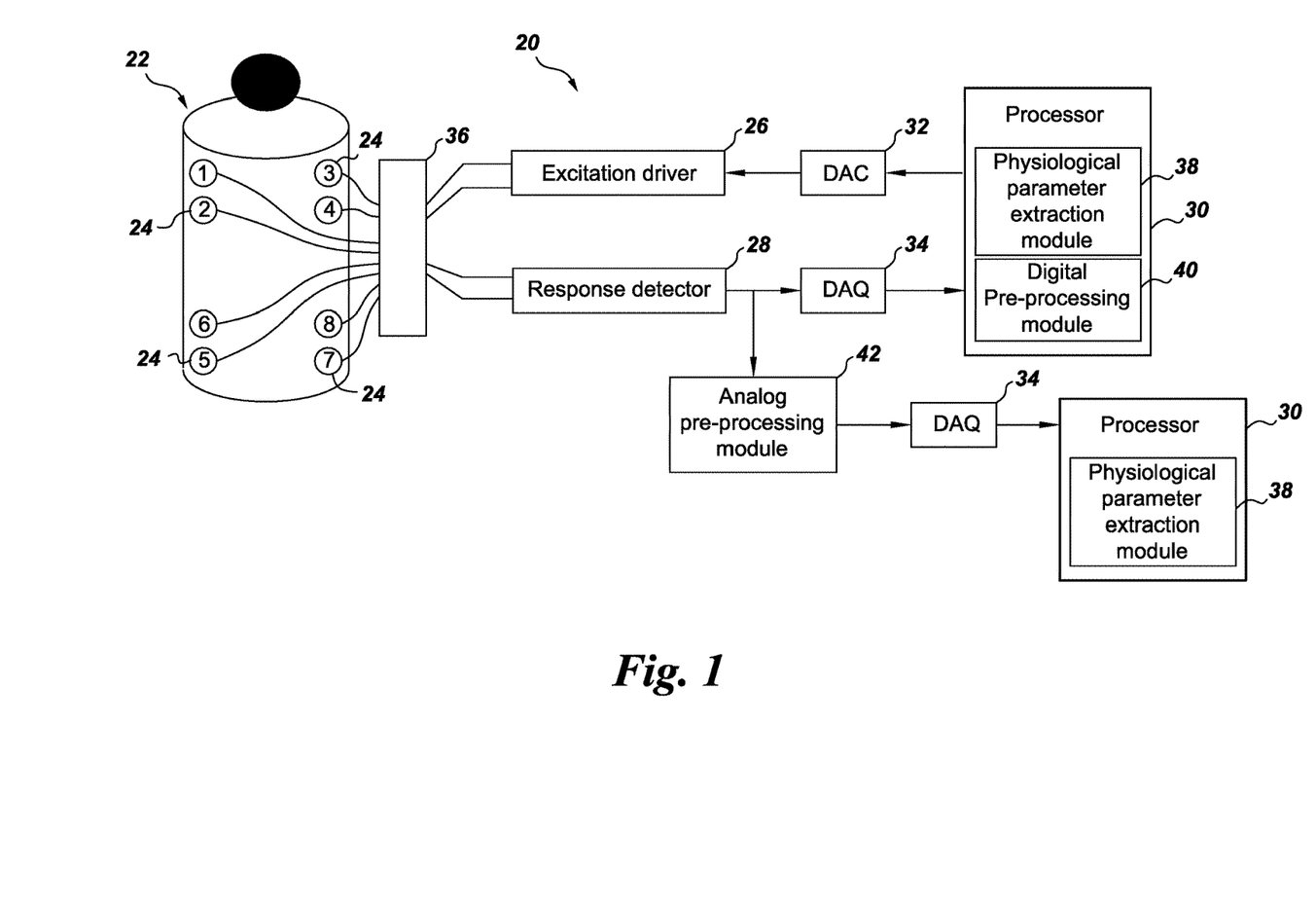
FIG. 1 is a simplified schematic block diagram illustrating an impedance measurement system formed in accordance with one embodiment.

One embodiment of an impedance measurement system 20 is illustrated in FIG. 1, which may be a transducer-based system, for example, an electrode-based system, such as a patient monitor that may form part of a patient monitoring device, such as an electrocardiography (ECG) monitoring device or an impedance cardiography module. However, the impedance measurement system 20 may also be an EIS/EIT system or another separate unit. The impedance measurement system 20 may be used to obtain electrical impedance measurements of an object 22 (e.g., a patient), which are used to separate physiological activities of interest from undesired physiological activities and non-physiological signals. For example, electrical impedance measurements obtained may be used in at least one embodiment to separate respiratory rate from patient motion.

In the illustrated embodiment, the impedance measurement system 20 includes a plurality of transducers 24, which may be a plurality of electrodes, positioned at or proximate a surface of the object 22, which in a healthcare application (e.g., patient monitoring) may include attaching the plurality of the transducers 24 to the skin of a patient or subject. It should be noted that although eight transducers 24 are illustrated, more or fewer transducers 24 may be used. It also should be noted that different types of transducers 24 may be used to generate different types of excitations, for example, in addition to current, other sources of excitation include voltage, magnetic fields or radio-frequency waves, among others. Thus, the transducers 24 also may be surface-contacting electrodes, standoff electrodes, antennas, and coils (e.g., conducting coils), among others. As other examples, the transducers 24 also may be capacitively coupled electrodes or ultrasound transducers, among others. For example, the transducers 24 may be positioned on the surface of the object 22 (e.g. electrodes, thermal sources, ultrasound transducers), near the surface of the object 22 (e.g., radiofrequency antenna), or penetrating the surface of the object 22 (e.g., needle electrodes).

The transducers 24 may be positioned at a surface of the object 22 in different arrangements and may be driven in different configurations. For example, the transducers 24 may be electrodes positioned at a surface of the object 22 using one of a plurality of standard or conventional ECG locations (e.g., Lead I, Lead II or Lead III ECG configurations). However, in other embodiments, different positioning of the transducers 24 in non-standard ECG locations may be provided (e.g., sub-axillary configurations). For example, the transducers 24 may be positioned to provide different views of trajectories/angles through the lungs and/or torso to provide increased sensitivity to breathing and decreased sensitivity to ambulatory motion. Additionally, combinations of the different positioning arrangements may be used such as having current driven transducers 24 in a Lead II configuration (right arm to left leg) and voltage measuring transducers 24 in a Lead I configuration (right arm to left arm), or vice versa. As other non-limiting examples of modification or variations, a configuration similar to the Lead II configuration may be provided, but with the right arm transducers 24 placed on the back of the shoulder (Lead II Back configuration) or with the current driven transducers 24 positioned in sub-axillary locations with voltage measurement transducers 24 on the front of the chest and center of the back.

Additionally, in various embodiments, the current driving one or more of the transducers 24 may be at the same carrier frequency, but with different phase (e.g., 0 degrees, 90 degrees, 180 degrees and 270 degrees). It should be noted that some of the transducers 24 may have no current applied thereto, but are used only for voltage measurements. It also should be noted that the frequency for the applied currents may be 10 kHz, however as should be appreciated, other frequencies may be used. It further should be noted that one or more of the transducers 24 may be a ground reference or a reference for current return and noise cancellation purposes.

Referring again to FIG. 1, the impedance measurement system 20 also includes an excitation driver 26 and a response detector 28 that are coupled to the transducers 24, and which are each connected to a processor 30 (e.g., a computing device). In one embodiment, the excitation driver 26 and the response detector 28 are physically separate devices. In other embodiments, the excitation driver 26 and the response detector 28 are physically integrated as one element. The processor 30 sends instructions to the excitation driver 26 through a digital to analog converter (DAC) element 32 and receives data from the response detector 28 through a data-acquisition (DAQ) element 34. It should be noted that one or more excitation drivers 26 may be provided, such that one is provided per transducer 24, for a subset of transducers 24 or for all transducers 24.

In certain embodiments as shown further in FIG. 1, the response detector can preprocess analog signals before digitization (42) by the DAQ (34) or it could be done after digitization. As such, preprocessing may be performed on either an analog signal or a digital signal obtained from the analog. While analog signal contains more complete information, digitization in certain embodiments, may maintain the critical parameters such that quality is not lost in the preprocessing step.

In various embodiments, a multi-wire measurement configuration is provided that uses different pairs of transducers 24 for excitation from the excitation driver 26 and measurement by the response detector 28. The connection also may be provided via an interface 36. Additionally, variations and modifications may be provided, such as using two-wire or four-wire configurations wherein the same pair of transducers 24 for excitation from the excitation driver 26 is used for measurement by the response detector 28.

The transducers 24 may be formed from any suitable conductive material used to establish a desired excitation. For example, the transducers 24 may be formed from one or more metals such as copper, gold, platinum, steel, silver, and alloys thereof. Other exemplary materials for forming the transducers 24 include non-metals that are electrically conductive, such as a silicon based materials used in combination with micro-circuits. In one embodiment, where the object 22 is a human body region, the transducers 24 are formed from silver-silver chloride. Additionally, the transducers 24 may be formed in different shapes and/or sizes, for example, as rod-shaped, flat plate-shaped, or needle-shaped structures. It should be noted that in some embodiments, the transducers 24 are insulated from one another. In other embodiments, the transducers 24 can be positioned in direct ohmic contact with the object 22 or capacitively coupled to the object 22.

In some embodiments, the transducers 24 are standard ECG electrodes having a surface area of about 1 square centimeter (sq. cm). However, different sized and shaped electrodes may be used, such as larger electrodes having a surface area of about or at least 70 sq. cm., where an increase in surface area may provide an increase in signal-to-noise ratio. However, the physiological parameter extraction of the various embodiments may be implemented in connection with any suitable size, shape or type of transducer 24.

In operation, the transducers 24 may be used to deliver electrical current continuously or modulated such that excitations may be applied across a temporal frequency range (e.g., 1 kHz to 1 MHz) to the surface of the object 22 to generate an electromagnetic (EM) field within the object 22. The resulting surface potentials, namely the voltages (real, imaginary or complex) on the transducers 24 are measured to determine an electrical impedance (e.g. electrical conductivity or permittivity distribution), which is used to separate or distinguish different physiological parameters.

Thus, in various embodiments, the excitation driver 26 applies an excitation current to one or more of the transducers 24 with a voltage response measured by one or more the transducers 24. A physiological parameter extraction module 38, which may be implemented, for example, as software within the processor 30 (or within hardware or a combination of software and hardware), then fits the multi-electrode array signals in one embodiment into a minimum-maximum (min-max) optimization algorithm using a sigma delta ($\Sigma\Delta$) modulator framework as described in more detail herein. In various embodiments, the framework may be embodied as a multiple-input-multiple-output (MIMO) processing 40, which may be a MIMO processing algorithm that reduces or minimizes the number of transducers 24 used to monitor respiratory rate. As such, in certain embodiments, the min-max optimization algorithm is not restricted to MIMO processing but can be generalized to analog/digital preconditioning followed by digital classifications (60).

In general, the MIMO processing 40 separates the spatial information of respiratory rate from temporal signals captured with a reduced or minimized number of transducers 24, such as impedance measurement electrodes. Thus, various embodiments provide signal conditioning and a data acquisition method or algorithm for the separation, characterization and/or event attribution of physiological signals captured using electrical impedance measurements in the presence of noise sources and motion artifacts. Respiratory rate may be spatial information seen across multiple transducers 24 within noise and/or motion artifacts. Thus, different responses including but not limited to impedance signals or impedance measurements are used in various embodiments to distinguish different physiological parameters, which correspond in some embodiments to breathing and ambulatory motion.

It should be noted that the various embodiments may be implemented, for example, in connection with different types of soft-field tomography systems, such as Electrical Impedance Spectroscopy (EIS), Electrical Impedance Tomography (EIT), Diffuse Optical Tomography (DOT), Near InfraRed Spectroscopy (NIRS), thermography, elastography, microwave tomography or microwave spectroscopy, and related modalities.

Various embodiments and methods generally use multiple electrical measurements (for example electrical measurements that are obtained from the plurality of transducers 24). It also should be noted that different measurements, such as different voltage, current, magnetic field, optical signal, radio-frequency (RF) wave, thermal field, mechanical deformation, ultrasound signal, or electrical impedance or permittivity measurements, among others, may be made.

Figure 2:
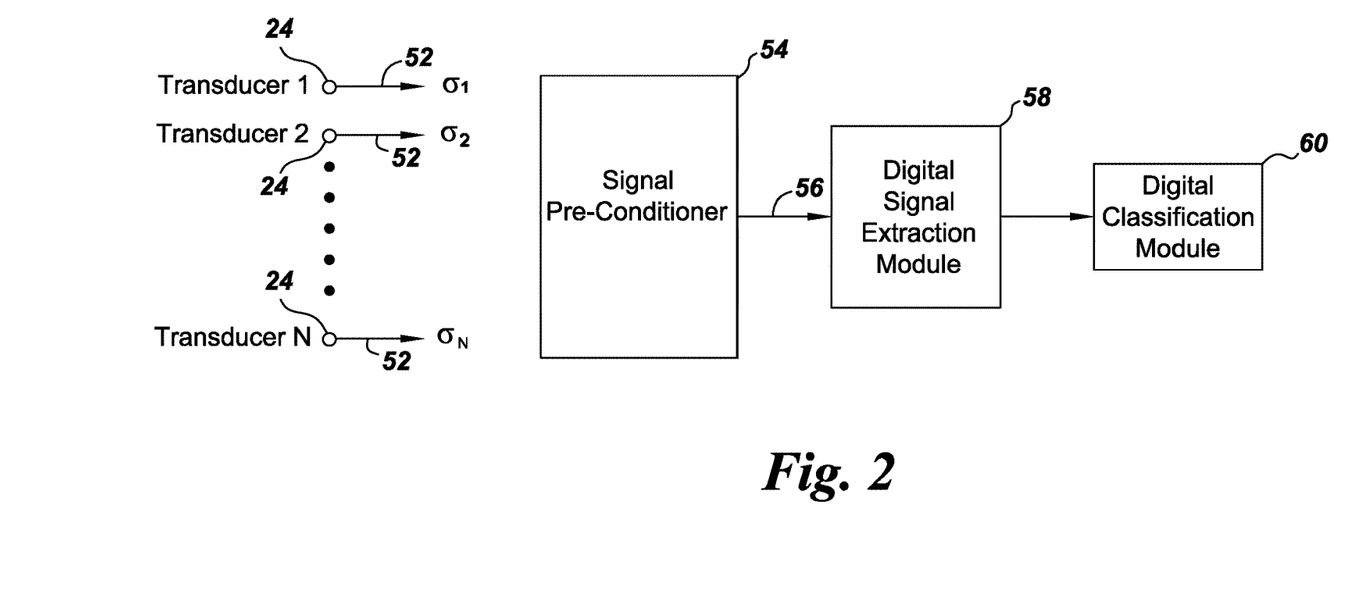
FIG. 2 is a simplified block diagram illustrating a physiological data extraction process performed in accordance with various embodiments.

Various embodiments and methods to separate or distinguish impedance signals will now be described in more detail. In particular a physiological data (or parameter) extraction process is illustrated in FIG. 2 multiple electrical measurements (e.g., electrical impedance measurements illustrated as measurement signals 52 ($\sigma_1, \sigma_2 \ldots \sigma_N$)) are obtained from the plurality of transducers 24. It should be noted that although the measurement signals are illustrated as electrical conductivity measurements of the object 22, different measurements, such as different voltage, current, magnetic field, radiofrequency (RF) wave, or electrical impedance measurements may be made, for example, electrical permittivity measurements.

In various embodiments, signals within in noise and dominant motion artifacts are separated and attributed to physiological events of interests such as breathing, motion, etc. The received measurements signals 52 are pre-conditioned using a signal pre-conditioner 54 (analog or digital), which in various embodiments includes using a spatial differentiation technique that reduces or eliminates common mode signals and enhances the quality of spatially correlated signals of interest. The output of the signal pre-conditioner 54, namely preconditioned signals 56 are fit into digital signal extraction module 58. In certain embodiments, this may be a MIMO processor 58 (e.g., embodied as the MIMO processor 40 of FIG. 1) (but not restricted to MIMO processing) that de-correlates the signals 56 and extracts spatial information, which may be used to classify the signals using a classification module 60. It should be noted that the MIMO architecture for the MIMO processor 58 may be implemented in different configurations (digital equivalentThe outputs of the MIMO array 58 in various embodiments include digitized de-correlation coefficients of the signals and an uncorrelated output data stream. The digitized de-correlation coefficients show the output stability marked by an index number. This digitized stability index shows the existence of signal correlation and accordingly spatial signal information. The common mode spatial signals are digitized through lower dimensional outputs, whereas higher dimensional channels reduce or minimize the energy of the signals indicating the degree of correlation among signals. In various embodiments, the relative energy of the digitized higher dimensional signals with respect to common mode signals is used as an indicator of motion artifacts, if any. It should be noted that in the absence of motion artifacts or body motion, the common mode signal represents the respiratory rate of the patient. Using a stability index of de-correlation coefficient, common mode signal and relative energy of lower dimensional channels, as described in more detail herein, various embodiments can classify a respiration pattern seen in a human subject such as normal breathing rate, distress conditions, breathing stoppage and body motion with breathing.

Thus, in operation, signals are acquired by the electrodes 24 (shown in FIG. 1), such as impedance based electrodes for respiratory rate monitoring, which are spatially differentiated to remove an unwanted common mode signal to improve the signal to noise ratio. The spatially differentiated signals are applied to the MIMO processor 40, the output of which includes de-correlation coefficients. The stability index of de-correlation coefficients, spatial signal information and the relative energy of the lower dimensional channels are then used to classify respiration pattern. Thus, various embodiments, instead of processing the received measurement signals, defines the spatial information as the fundamental signal of interest, such that the common mode signals are separated in the analog domain before digitization to obtain direct information with respect to spatial features attributed to biological events of interest.

Figure 3:
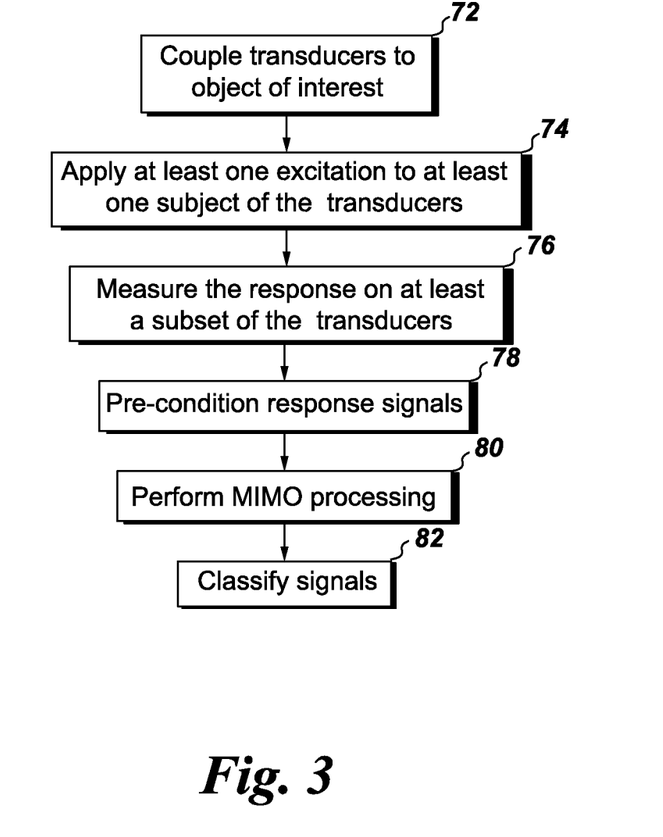
FIG. 3 is a flowchart of a method in accordance with various embodiments to extract physiological parameters from electrical measurements.

In accordance with various embodiments, a method is performed to extract physiological parameters from electrical measurements as shown in FIG. 3. In particular, a plurality of transducers, for example in this embodiment a plurality of electrodes (e.g., eight electrodes), are coupled (e.g., applied) to an object of interest (e.g., a body or volume of interest) at 72. In some embodiments, such as when monitoring a patient, a plurality of electrodes may be applied to the skin of the thorax of the patient. As described herein, different configurations of electrode positioning may be provided, such as using standard ECG lead positioning. In general, various embodiments apply multi-lead electrodes that are used to extract respiratory information from motion artifacts as described in more detail below, in particular, spatially distributed multi-lead impedance measurements are performed such that using reference measurements (a priori information), breathing motion is separated from ambulatory motion. Thus, using the method 70, continuous, real-time and power-efficient tracking of the respiratory signal embedded in a multi-dimensional signal-space corrupted by motion artifacts may be provided.

Thereafter, in one exemplary embodiment, at least one excitation, for example, electrical currents are applied to at least a subset of the transducers, for example, one or more of the electrodes at 74. For example, a low level current, such as an EIS/EIT suitable current is applied to one or more of the electrodes. Thereafter, in this embodiment, a response, for example, electrical voltages are measured on at least a subset of the transducers, for example, one or more of the electrodes at 76. In some embodiments the electrical voltages are measured simultaneously or concurrently on all of the electrodes. The electrode measurements in these embodiments, when taken in the context of the applied excitations, correspond to a measured electrical conductivity of the patient, which can change, for example, during breathing. For example, air entering and exiting the lungs can change the resistance to current through the patient.

The response signals are then pre-conditioned at 78. In particular, the pre-conditioning includes spatially separating the responses using spatial variation information, such as by using responses from simultaneous excitations of at least a subset of the electrodes using different phases. In one embodiment, an average from all of the responses (common mode) may be used in a subtraction process to pre-condition the signals to provide signal separation. For example, the mean or common mode may be subtracted from the response signals. Thus, motion is localized to differentiate local information from spatial information. Accordingly, the pre-conditioning of the response signals at 78 is a spatial pre-conditioning that converts the response signals into spatial vectors.

Thereafter, the pre-conditioned signals are applied to a MIMO processor at 80 to identify a correlated signal. For example, the pre-conditioned signals (which are pre-conditioned analog signals) define input vectors to the MIMO processor, which are then transformed, for example, using a suitable linear transformation matrix. The preconditioned signals could be in analog or digital form. In certain embodiments, the preconditioned analog signals are digitized before they are processed by a digital classifier. The linear transformation matrix is formed to increase or maximize the de-correlation between the signals in the input vectors. The transformed input vectors are then converted to digital data using one or more sigma delta converters.

In certain embodiments, the fundamental architecture of the device comprises four modules; a transducer array, signal pre-processor, signal post-processor and signal analyzer/classifier. The transducer array is stimulated by sourcing current through transducer array through the use of a digital pattern generator followed by a Digital to Analog converter (DAC). As such, in certain embodiments the transducers convert impedance into measurable analog signals. These analog signals, in certain embodiments, may be pre-processed to remove at least one of signal offset, spatial differentiation, common mode remove, or a combination thereof. The signals may be filtered to remove high frequency noise.

In certain embodiments, these pre-processed signals are processed using digital signal processing algorithms for feature extraction followed by digital classifier to track breathing rate and activity motion index.

Of the four modules, in certain embodiments, only the transducer array module signals remain in analog form. The classifier module has digital form. Therefore, in certain embodiments, the signal pre-processor and post-processor can be analog or digital.

In an alternative embodiment, the MIMO processor is an example where transducer signal acquisition and signal pre-processing remains in analog domain and then digitally post processed before analysis and or data classification.

As such, the two prior examples demonstrate the signal modules can change to analog/digital form based on many factors, including but not limited to analog/digital power, form factor, data transfer rate, communication protocol, quantization efficiency, SNR, or a combination thereof.

In certain embodiments, the digital data may be used at 82 to classify the signals. For example, different signal energy levels or patterns may be used to classify the signals as breathing signals or breathing and localized body motion signals. As such, the digital signals may be used to identify physiological or non-physiological parameters of interest, such that breathing and ambulatory motion signals may be separated and identified. Accordingly, the breathing rate of a moving patient may be monitored.

Figure 4:
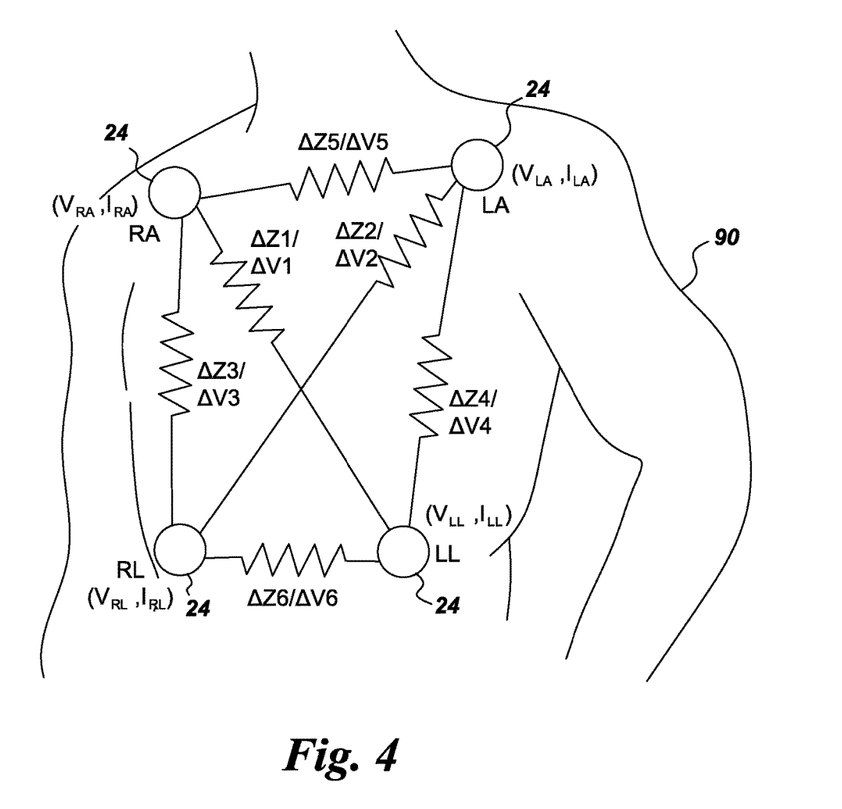
FIG. 4 is a diagram illustrating transducer placement in accordance with an embodiment.
Figure 5:
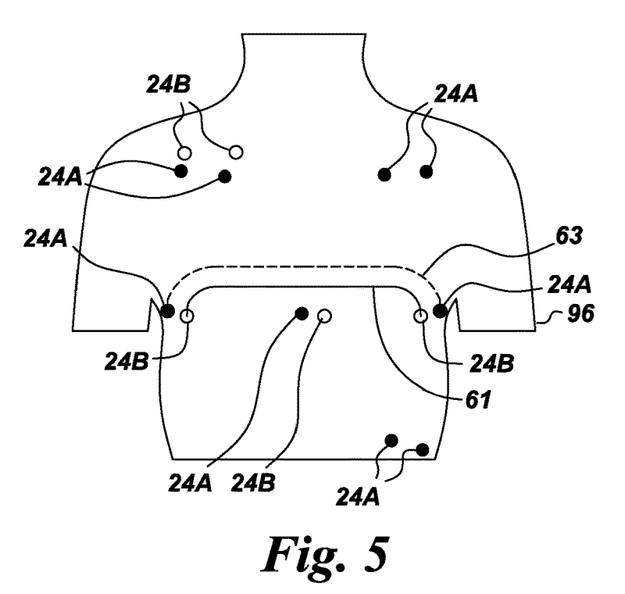
FIG. 5 is a diagram illustrating transducer placement in accordance with another embodiment.
Figure 6:
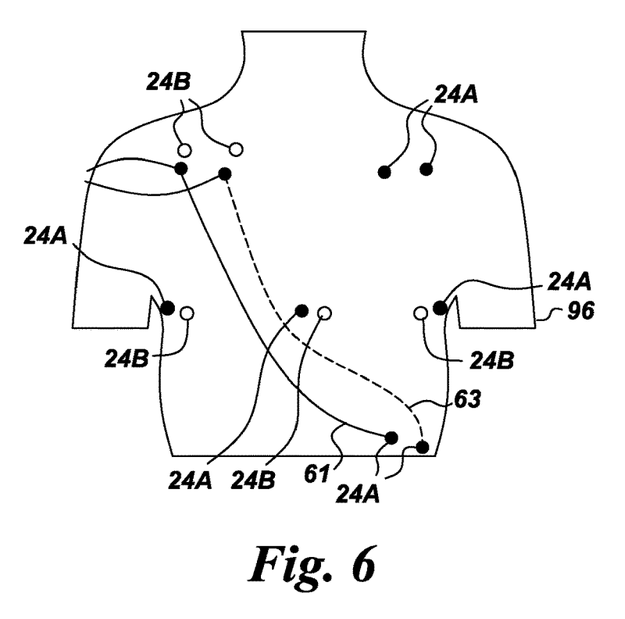
FIG. 6 is a diagram illustrating transducer placement in accordance with another embodiment.
Figure 7:
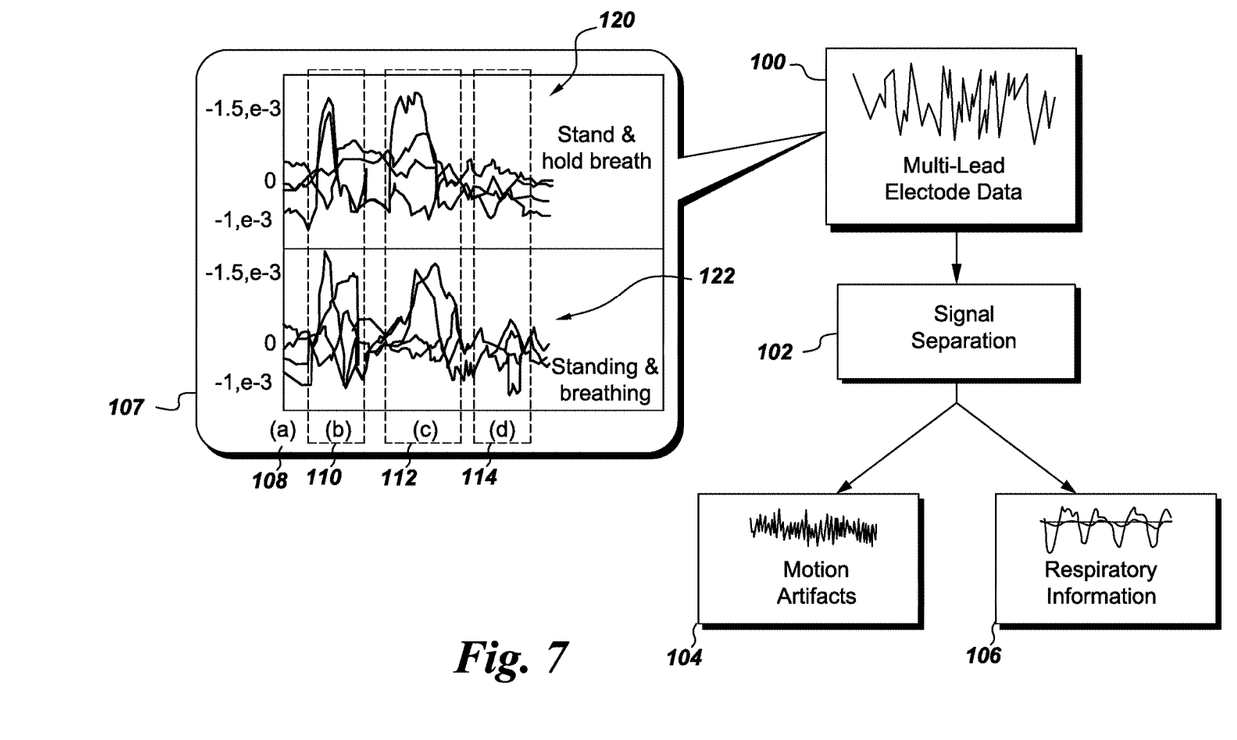
FIG. 7 is a diagram illustrating signal separation in accordance with various embodiments for different types of motion signals.

Various embodiments may provide different configurations of lead placements as shown in FIGS. 4 through 6. As an example, and in one embodiment, a set of four transducers 24 (e.g., electrodes) are placed on the thorax of a patient 90 as shown in FIG. 4, thereby defining a multi-lead electrode placement. In this configuration, the differential impedance measured across the multi-lead electrodes represents the spatially distributed respiratory information along with motion artifacts. For example, as illustrated in FIG. 7, multi-lead electrode data 100 may be processed using signal separation techniques 102 as described in more detail herein to obtain motion artifact signals 104 and respiratory information signals 106.

The graph 107 shown examples of localized motion artifacts captured by multi-lead electrodes when the patient 90 (shown in FIGS. 4 through 6) performs different activities while standing and breath holding or standing and breathing as illustrated by the signals 120 and 122, respectively. In particular, the potion 108 of the signals 120 and 122 is when the patient is still (no motion), the portion 110 is when the patient picks up an object (e.g., on a desk), the portion 112 is when the patient reaches for an object (e.g., reaches for a shelf) and the portion 114 is when the patient walks and turns in place.

The differences in the behavior or responses of the impedance changes between multiple electrodes of the non-stationary multi-lead signals may be used to identify different types of motion (e.g., breathing, bending, twisting, reaching) or of non-motion (e.g., patient is still) in different positions, for example, supine, seated and standing positions.

It should be noted that different transducer configurations may be used to acquire response data. For example, eight electrodes may be placed on the thorax with two electrodes nearby each other in each of the traditional ECG locations including the Right Arm, Left Arm, Right Leg, and Left Leg locations. As another example, FIG. 5 illustrates a sub-axillary electrode placement configuration in accordance with one embodiment and FIG. 6 represents a Lead II electrode placement configuration, both on a human thorax 96. It should be noted that the front electrodes are identified by transducers 24a and the back electrodes are identified by transducers 24b. It also should be noted that the solid line represents an exemplary current path and the dashed line represents a corresponding exemplary measured voltage.

In this illustrative embodiment, one transducer 24 of each pair of transducers 24 drives a small AC current (e.g., 60 μA) at a carrier frequency (e.g., 10 kHz) and the other transducer 24 of each pair does not drive current. The current path is represented by path 61. Thereafter, voltage measurements are performed for all transducers 24 including the current driving transducers 24 and the non-current driving transducers 24. The voltage measurement path is illustrated by path 63. The voltage measurements in various embodiments may be performed using a matched filter (at the carrier frequency) to provide an amplitude and phase or real and imaginary measurement.

Figure 8:
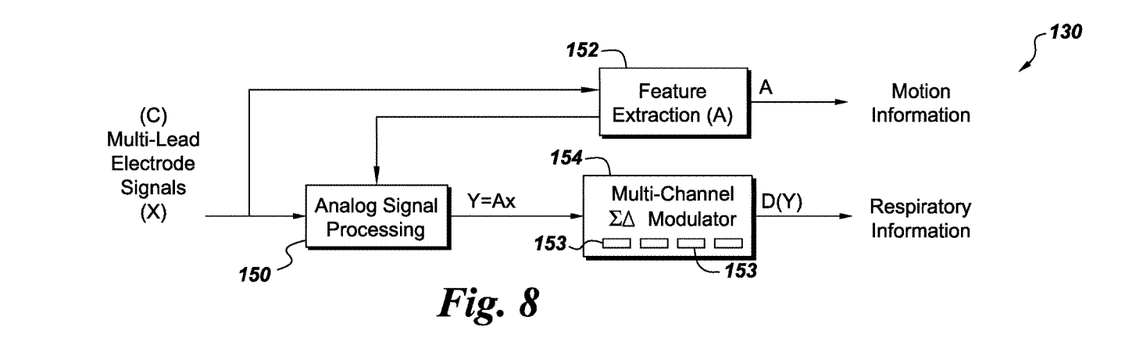
FIG. 8 is a block diagram illustrating an architecture for respiratory rate monitoring in accordance with various embodiments.

Thus, in accordance with various embodiments, an architecture 130 as shown in FIG. 8 may be used for respiratory rate monitoring. In particular, the desired respiratory signal occupies a sub-space within the high dimensional space spanned by the multi-lead electrode signals (e.g., represented by the multi-lead electrode data 100 shown in FIG. 7). The architecture 130 may in various embodiments provides a real-time adaptive learning method or technique that uses the spatial correlation of signals to separate respiratory information from motion artifacts. In particular, the MIMO based respiratory monitoring in various embodiments first identifies and then tracks the sub-space spanned by the respiratory signals and cancels out motion artifacts and cross-channel redundancy.

The architecture 130 in one embodiment includes an analog matrix-vector multiplier (shown as analog signal processing 150) that transforms the multi-lead measurements x (in particular the differential voltages ΔV as shown in FIG. 4) according to the following:

$$Z = Ax \quad \text{Eq. 1}$$

where A is a lower-triangular transformation matrix.

Thus, a feature extraction 152 is provided. An array of parallel sigma-delta sigma delta (ΣΔ) modulators 153 illustrated as a multichannel sigma delta (ΣΔ) modulator 154 then produces an output digital sequence encoding y of the transformed multi-lead electrode signal z. In one embodiment, the one-bit digital sequence is used in various embodiments for online continuous adaption of the matrix A according to an anti-Hebbian rule such that the digitized output sequence y is uncorrelated with respect to each other. For multi-lead measurements, the signal transformation implies separating the common-mode respiratory signal from other signals that contain motion artifacts.

Figure 9:
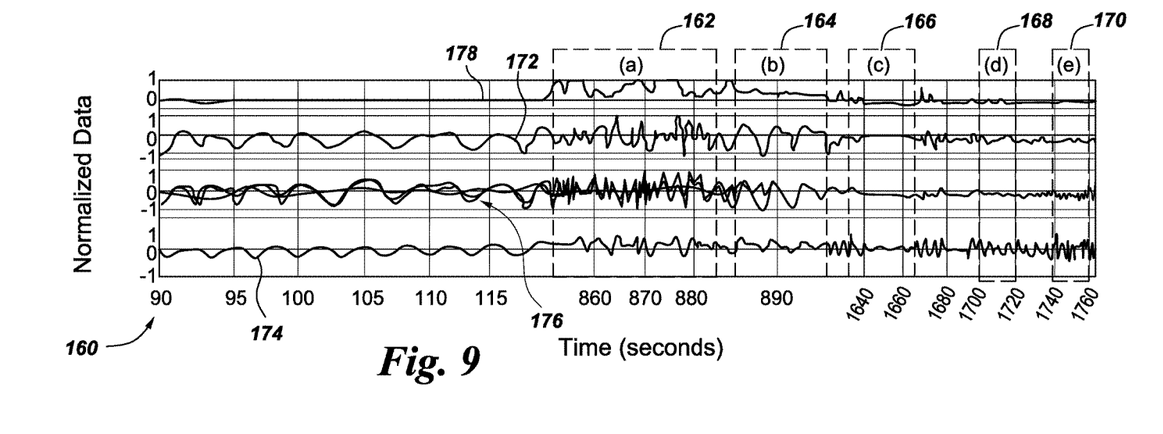
FIG. 9 is a graph illustrating output signals generated using various embodiments for extracting respiratory/breathing data along with motion/activity index information.

Thus, various embodiments may acquire ambulatory human subject data using a multi-lead measurement system, which may have a standard or conventional lead placement configuration. FIG. 9 is a graph 160 illustrating the results of various embodiments using signal pre-conditioning and MIMO processing for extracting respiratory/breathing data along with motion/activity index information for conditions of normal breathing, as well as patient motion (illustrated in the portion 162), deep breathing (illustrated in the portion 164), apnea (illustrated in the portion 166), shallow breathing (illustrated in the portion 168), and fast breathing (illustrated in the portion 170). The illustrated signals are merely exemplary. As can be seen, in the absence of motion artifacts, the primary channel (illustrated by the signal 172, which is the outputs of the MIMO processor) tracks the referenced spirometer signal (illustrated by the signal 174), while the other channels (illustrated by the signal 176) achieve a minimal energy state, thereby inferring the presence of minimal motion artifacts. It should be noted that the MIMO architecture also provides non-respiratory motion information shown by the ambulatory motion index (illustrated by the signal 178). The ambulatory motion index in various embodiments is defined by the ratio of the energy of channel 1 (signal 172) to the energy of the remaining channels (signals 176). Thus, if all channels only include a breathing signal, the ambulatory motion index is a zero signal.

In accordance with some embodiments, a multi-level monitoring approach may be provided. For example, the channel 1 signal (signal 172) may be used as a threshold. In particular, if only breathing is detected, then the data from the remaining channels (signals 176) may be weighted less in classifying the current breathing condition of the patient. However, if motion is detected, then there is less confidence in the breathing signal and the signals from the remaining channels (signals 176) are given more weight. Thus, the channel 1 signal (signal 172) tracks a breathing rate, which is supplemented by the ambulatory motion index. It should be noted that this is the case when some breathing is detected. Accordingly, using this monitoring approach different warnings or notifications (e.g., visual or audible notifications) may be provided.

Thus, various embodiments provide a motion canceling MIMO method for ambulatory rate monitoring.

Additionally, although the various embodiments are described in connection with electrical (current and voltage) excitation, other sources of excitation may be provided. For example, magnetic, or radio-frequency (RF) excitations, among others, may be used in combination with the various embodiments. Thus, the measured responses are not limited to electrical responses, but may be, for example, magnetic or RF responses.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for separating measurement signals, the method comprising:
   coupling a plurality of transducers on a surface of an object, the plurality of transducers comprising at least two excitation transducers and at least two measuring transducers;
   generating excitations on at least a subset of the plurality of transducers, the excitations driven in different configurations from at least one of the two excitation transducers;
   obtaining measurement response signals at a response detector, as acquired from the subset of the plurality of transducers an analog format;
   spatially pre-conditioning the measurement response signals to convert the measurement response signals into spatial vectors;
   performing multiple-input-multiple-output (MIMO) processing of the spatial vectors to separate the measurement signals of a sub space of desired physiological activities, as distinguished from a sub-space of undesired non-physiological signals; where the processing comprises identifying and tracking the sub-space of desired physiological activities; and
   classifying the measurement signals of the sub-space of desired physiological activities as respiratory information and classifying the sub-space undesired non-physiological signals as ambulatory, motion information.

2. The method of claim 1, wherein the measurement response signals are electrical measurement response signals.

3. The method of claim 2, wherein spatially pre-conditioning the obtained electrical measurement response signals comprises using a common mode averaging of all of the electrical measurement response signals.

4. The method of claim 2, wherein the electrical measurement response signals are obtained from electrodes in an electrocardiography (ECG) electrode placement configuration.

5. The method of claim 2, wherein the excitations comprises one of an electrical, magnetic, or radio-frequency excitation.

6. The method of claim 5, wherein obtaining the electrical measurement response signals composes measuring at least one of an electrical voltage, current, magnetic response or radio-frequency response on all or a subset of the plurality of transducers.

7. The method of claim 1, wherein classifying the sub-space of undesired non-physiological signals as ambulatory motion information includes identifying at least one of a type of motion or a position.

8. The method of claim 7, wherein the ambulatory motion information includes an identification of at least one of breathing, bending, twisting, or reaching motion.

9. The method of claim 8 wherein the ambulatory motion intimation includes an identification of at least one of a supine position, seated position, or standing.

10. The method of claim 1, further comprising using an output of the MIMO processor and multi-lead transducer signals to determine an ambulatory motion index.

11. A method for monitoring breathing, the method comprising:
    positioning a plurality of transducers on a surface of a person, the plurality of transducers comprising at least two excitation transducers and at least two measuring transducers;
    generating excitations on at least a subset of the plurality of transducers, the excitations driven in different configurations from at least one of the two excitation transducers;
    obtaining measurement response signals at a response detector, as acquired from all or the subset of the plurality of transducers;
    spatially pre-conditioning the obtained measurement response signals to convert the measurement response signals into spatial vectors:
    performing multiple input multiple output (MIMO) processing of the spatial vectors to separate the measurement response signals of a sub-space of desired physiological activites, as distinguished from a sub-space of undesired non-physiological signals; where the processing comprises identifying and tracking the sub-space of desired physiological activities; and
    classifying the measurement signals of the sub-space of desired physiological activities as respiratory information and classifying the sub-space undesired non-physiological signals as ambulatory motion information.

12. The method of claim 11, further comprising preconditioning the measurement signals prior to performing the processing with the MIMO processor.

13. The method of claim 12, wherein the measurement signals are obtained simultaneously or sequentially.

14. The method of 12, wherein the output of the processing with the MIMO processor comprises digitized de-correlation coefficients of the spatial vectors and an uncorrelated output data stream.

15. The method of claim 11, further comprising using an output of the MIMO processing and multi-lead transducer signals to determine an ambulatory motion index.

16. The method of claim 15, further comprising using the ambulatory motion index and the separated measurement signals in a weighting process to classify different types of breathing.

* * * * *